US008915977B2

(12) United States Patent
Fang et al.

(10) Patent No.: US 8,915,977 B2
(45) Date of Patent: Dec. 23, 2014

(54) GASOLINE FUEL COMPOSITION FOR IMPROVED PERFORMANCE IN FUEL INJECTED ENGINES

(71) Applicant: Afton Chemical Corporation, Richmond, VA (US)

(72) Inventors: Xinggao Fang, Midlothian, VA (US); Scott D. Schwab, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 102 days.

(21) Appl. No.: 13/871,482

(22) Filed: Apr. 26, 2013

(65) Prior Publication Data
US 2014/0318486 A1 Oct. 30, 2014

(51) Int. Cl.
| | | |
|---|---|---|
| C10L 1/22 | (2006.01) |
| C10L 1/222 | (2006.01) |
| C07C 233/38 | (2006.01) |
| C07C 233/89 | (2006.01) |
| C10L 1/14 | (2006.01) |
| C10L 1/224 | (2006.01) |
| C10L 1/238 | (2006.01) |
| C10L 10/04 | (2006.01) |
| C10L 10/06 | (2006.01) |
| C10L 1/183 | (2006.01) |
| C10L 1/188 | (2006.01) |
| C10L 1/198 | (2006.01) |

(52) U.S. Cl.
CPC ............... *C10L 1/222* (2013.01); *C07C 233/38* (2013.01); *C07C 233/89* (2013.01); *C10L 1/14* (2013.01); *C10L 1/143* (2013.01); *C10L 1/224* (2013.01); *C10L 1/238* (2013.01); *C10L 10/04* (2013.01); *C10L 10/06* (2013.01); *C10L 1/2222* (2013.01); *C10L 1/1832* (2013.01); *C10L 1/1881* (2013.01); *C10L 1/198* (2013.01); *C10L 2200/0423* (2013.01)

USPC ............................................................ 44/422

(58) Field of Classification Search
CPC ..................................................... C10L 1/2222
USPC ............................................................ 44/422
See application file for complete search history.

(56) References Cited

U.S. PATENT DOCUMENTS

| | | | |
|---|---|---|---|
| 2,589,674 A | 3/1952 | Cook et al. | |
| 3,401,119 A * | 9/1968 | Froehlich ................. | 510/481 |
| 4,180,643 A | 12/1979 | Moss et al. | |
| 4,482,357 A | 11/1984 | Hanlon | |
| 4,621,141 A | 11/1986 | Chibnik | |
| 4,631,071 A | 12/1986 | Axelrod et al. | |
| 4,657,562 A | 4/1987 | Axelrod et al. | |
| 6,964,940 B1 * | 11/2005 | Treybig et al. .............. | 507/129 |
| 7,947,093 B2 * | 5/2011 | Barton et al. ................ | 44/422 |
| 8,147,569 B2 | 4/2012 | Barton et al. | |
| 2008/0113890 A1 | 5/2008 | Moreton et al. | |
| 2011/0258917 A1 | 10/2011 | Garcia et al. | |
| 2012/0010112 A1 | 1/2012 | Grabarse et al. | |
| 2012/0138004 A1 | 6/2012 | Stevenson et al. | |
| 2013/0031827 A1 | 2/2013 | Reid et al. | |
| 2013/0031828 A1 | 2/2013 | Reid et al. | |

FOREIGN PATENT DOCUMENTS

| | | |
|---|---|---|
| EP | 0336267 A2 | 10/1989 |
| WO | 2011149799 A1 | 12/2011 |

\* cited by examiner

*Primary Examiner* — Cephia D Toomer
(74) *Attorney, Agent, or Firm* — Luedeka Neely Group, P.C.

(57) ABSTRACT

A fuel soluble additive for a gasoline engine, a method for improving performance of fuel injectors and a method for cleaning fuel injectors for a gasoline engine. The fuel soluble additive includes a quaternary ammonium salt derived from an amido amine containing at least one tertiary amino group and an epoxide, in the presence of a proton donor selected from a carboxylic acid and an alkyl phenol. The amido amine is made in a reaction medium that is substantially devoid of an acylating agent.

19 Claims, No Drawings

GASOLINE FUEL COMPOSITION FOR IMPROVED PERFORMANCE IN FUEL INJECTED ENGINES

TECHNICAL FIELD

The disclosure is directed to gasoline fuel additives and to additive and additive concentrates that include the additive that are useful for improving the performance of gasoline fuel injected engines. In particular, the disclosure is directed to additives for port fuel injection gasoline engines as well as direct injection gasoline (DIG) engines.

BACKGROUND AND SUMMARY

It has long been desired to maximize fuel economy, power and driveability in gasoline powered vehicles while enhancing acceleration, reducing emissions, and preventing hesitation. While it is known to enhance gasoline powered engine performance by employing dispersants to keep valves and fuel injectors clean in port fuel injection engines, such gasoline dispersants are not necessarily effective for cleaning up direct fuel injected engines.

With the current use of direct fuel injected gasoline engines, dispersants that previously could have been used for gasoline engines do not work for both direct injected engines and port fuel injected engines. For example Mannich dispersants that were used in port fuel injected gasoline engines fail to provide suitable improvement in direct injected gasoline engines.

Over the years, dispersant compositions for gasoline fuels have been developed. Dispersant compositions known in the art for use in fuels include compositions that may include polyalkylene succinimides, polyalkenepolyamines, polyetheramines, and polyalkyl substituted Mannich compounds. Dispersants are suitable for keeping soot and sludge suspended in a fluid, however the foregoing dispersants are not particularly effective for cleaning surfaces of direct fuel injected engines.

Hence, fuel compositions for direct fuel injected engines often produce undesirable deposits in the internal engine surfaces and fuel filters. Accordingly, improved compositions that can prevent deposit build up, maintaining "as new" cleanliness for the vehicle life are desired. Ideally, the same composition that can clean up dirty fuel injectors restoring performance to the previous "as new" condition would be equally desirable and valuable in the attempt to reduce air borne exhaust emissions and to improve the power performance of the engines.

In accordance with the disclosure, exemplary embodiments provide a fuel soluble additive for a gasoline engine, a gasoline fuel containing the additive, a method for improving performance of fuel injectors and a method for cleaning fuel injectors for a gasoline engine. The fuel soluble additive includes a quaternary ammonium salt derived from an amido amine containing at least one tertiary amino group and an epoxide, in the presence of a proton donor. The amido amine is made in a reaction medium that is substantially devoid of an acylating agent.

Another embodiment of the disclosure provides a gasoline fuel composition that includes from 5 to about 100 ppm based on a total weight of the fuel composition of a quaternary ammonium salt derived from an amido amine containing at least one tertiary amino group and an epoxide, in the presence of a proton donor selected from a carboxylic acid and an alkyl phenol. The amido amine is made in a reaction medium that is substantially devoid of an acylating agent.

A further embodiment of the disclosure provides a method improving the injector performance of a direct fuel injected gasoline (DIG) engine. The method includes operating the engine on a fuel composition containing a major amount of gasoline fuel and from about 5 to about 100 ppm by weight based on a total weight of the fuel composition of a quaternary ammonium salt derived from an amido amine containing at least one tertiary amino group and an epoxide, in the presence of a proton donor selected from a carboxylic acid and an alkyl phenol. The amido amine is made in a reaction medium that is substantially devoid of an acylating agent.

A further embodiment of the disclosure provides a method of operating a direct fuel injected gasoline (DIG) engine. The method includes combusting in the engine a fuel composition comprising a major amount of gasoline fuel and from about 5 to about 100 ppm by weight based on a total weight of the fuel composition of a quaternary ammonium salt derived from an amido amine containing at least one tertiary amino group and an epoxide, in the presence of a proton donor selected from a carboxylic acid and an alkyl phenol. The amido amine is made in a reaction medium that is substantially devoid of an acylating agent.

In another embodiment of the fuel additive is an amido amine derived from a fatty acid.

An advantage of the fuel additive described herein is that the additive may not only reduce the amount of deposits forming on fuel injectors, but the additive may also be effective to clean up dirty fuel injectors sufficient to provide improved engine performance.

Another advantage of the fuel additive described herein is that it may be used at a much lower concentration than a quaternary ammonium salt derived from an acylating agent, yet provide better injector cleanliness performance than conventional quaternary ammonium salts made from amines derived from acylating agents.

Additional embodiments and advantages of the disclosure will be set forth in part in the detailed description which follows, and/or can be learned by practice of the disclosure. It is to be understood that both the foregoing general description and the following detailed description are exemplary and explanatory only and are not restrictive of the disclosure, as claimed.

DETAILED DESCRIPTION OF EXEMPLARY EMBODIMENTS

The additive component of the disclosure may be used in minor amounts in a major amount of fuel and may be added to the fuel directly or added as a component of an additive concentrate to the fuel. A particularly suitable fuel additive component for improving the operation of internal combustion engines may be made by reacting a tertiary amine of the formula

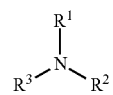

wherein each of $R^1$, $R^2$, and $R^3$ is selected from hydrocarbyl groups containing from 1 to 50 carbon atoms, with a carboxylic acid containing from 1 to 54 carbon atoms and a quaternizing agent to provide an alkoxylated quaternary ammonium salt. The reaction may be conducted in the presence of a protonating agent such as a carboxylic acid or an alkyl phenol. The alkoxylated quaternary ammonium salt may also be derived from an amido amine and a quaternizing agent in the presence of a protonating agent. The protonating agent may be obtained from a carboxylic acid, an alkyl phenol or from the amido amine wherein the reaction product containing the amido amine has an acid number ranging from about 1 to about 200 mg KOH/g. Regardless of how the alkoxylated quaternary ammonium salt is made, a key feature of the disclosure is that the amine contains at least one tertiary amino group and the amine is made in a reaction medium that is substantially devoid of an acylating agent.

As used herein, the term "hydrocarbyl group" or "hydrocarbyl" is used in its ordinary sense, which is well-known to those skilled in the art. Specifically, it refers to a group having a carbon atom directly attached to the remainder of a molecule and having a predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, amino, alkylamino, and sulfoxy);

(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as carbonyl, amido, imido, pyridyl, furyl, thienyl, ureyl, and imidazolyl. In general, no more than two, or as a further example, no more than one, non-hydrocarbon substituent will be present for every ten carbon atoms in the hydrocarbyl group; in some embodiments, there will be no non-hydrocarbon substituent in the hydrocarbyl group.

As used herein, the term "major amount" is understood to mean an amount greater than or equal to 50 wt. %, for example from about 80 to about 98 wt. % relative to the total weight of the composition. Moreover, as used herein, the term "minor amount" is understood to mean an amount less than 50 wt. % relative to the total weight of the composition.

As used herein the term "substantially devoid of an acylating agent" means that the reaction product is made in the absence or substantial absence of a reaction product of a long chain hydrocarbon, generally a polyolefin substituted with a monounsaturated carboxylic acid reactant such as (i) α,β-monounsaturated $C_4$ to $C_{10}$ dicarboxylic acid such as fumaric acid, itaconic acid, maleic acid; (ii) derivatives of (i) such as anhydrides or $C_1$ to $C_5$ alcohol derived mono- or di-esters of (i); (iii) α,β-monounsaturated $C_3$ to $C_{10}$ monocarboxylic acid such as acrylic acid and methacrylic acid; or (iv) derivatives of (iii) such as $C_1$ to $C_5$ alcohol derived esters of (iii) with any compound containing an olefinic bond represented by the general formula:

$$(R^4)(R^5)C=C(R^6)(CH(R^7)(R^8))$$

wherein each of $R^4$ and $R^5$ is, independently, hydrogen or a hydrocarbon based group. Each of $R^6$, $R^7$ and $R^8$ is, independently, hydrogen or a hydrocarbon based group; preferably at least one is a hydrocarbon based group containing at least 20 carbon atoms. Thus quaternized ammonium derivatives of acylating agents, such as described in U.S. Pat. Nos. 7,947, 0931; 7,951,211; and 8,147,569 are shown herein to be less effective in power recovery than the recovery attained by the additives described herein.

Amine Compound

In one embodiment, a tertiary amine including diamines and polyamines may be reacted with a C1 to C54 fatty acid to form an amido amine and the amido amine may be subsequently reacted with a quaternizing agent. Suitable tertiary amido amine compounds of the formula

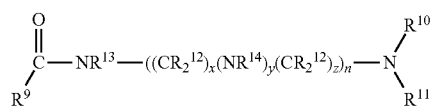

may be used, wherein each of $R^{10}$, and $R^{11}$ is selected from hydrocarbyl groups containing from 1 to 50 carbon atoms, each $R^9$, $R^{12}$, $R^{13}$ and $R^{14}$ may be independently selected from hydrogen or a hydrocarbyl group, x may range from 1 to 6, y may be 0 or 1, z may be 1 to 6, and n may range from 1 to 6. Each hydrocarbyl group $R^9$ to $R^{14}$ may independently be linear, branched, substituted, cyclic, saturated, unsaturated, or contain one or more hetero atoms. Suitable hydrocarbyl groups may include, but are not limited to alkyl groups, aryl groups, alkylaryl groups, arylalkyl groups, alkoxy groups, aryloxy groups, amino groups, and the like. Particularly suitable hydrocarbyl groups may be linear or branched alkyl groups. A representative example of an amine reactant which may be amidized and quaternized to yield compounds disclosed herein include for example, but are not limited to, dimethyl amino propyl amine.

If the amine contains solely primary or secondary amino groups, it may be desirable to alkylate at least one of the primary or secondary amino groups to a tertiary amino group prior to quaternizing the amine. In one embodiment, alkylation of primary amines and secondary amines or mixtures with tertiary amines may be exhaustively or partially alkylated to a tertiary amine and further alkoxylated to a quaternary salt.

Carboxylic Acid

When the amine has a primary or secondary amine group, the amine may be converted to an amido amine by reacting the amine with a $C_1$ to $C_{54}$ carboxylic acid. The acid may be a monoacid, a dimer acid, or a trimer acid. The acid may be selected from the group consisting of formic acid, acetic acid, propionic acid, butyric acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and the dimer and trimer acids thereof. When reacted with the amine, the reaction product may be a $C_1$-$C_{54}$-alkyl or alkenyl-substituted amido amine such as a $C_1$-$C_{54}$-alkyl or alkenyl-substituted amido propyldimethylamine.

Quaternizing Agent

A suitable quaternizing agents may be selected from the group consisting hydrocarbyl epoxides of the formula:

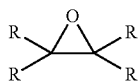

wherein each R is independently selected from H and a $C_1$ to $C_{50}$ hydrocarbyl group, and polyepoxides. Non-limiting examples of suitable epoxides that may be used as quaternizing agents may be selected from the group consisting of:
1,3-Butadiene diepoxide
Cyclohexene oxide
Cyclopentene oxide
Dicyclopentadiene dioxide
1,2,5,6-Diepoxycyclooctane
1,2,7,8-Diepoxyoctane
1,2-Epoxybutane
cis-2,3-Epoxybutane
3,4-Epoxy-1-butene
3,4-Epoxycyclohexylmethyl 3,4-epoxycyclohexanecarboxylate
1,2-Epoxydodecane
1,2-Epoxyhexadecane
1,2-Epoxyhexane
1,2-Epoxy-5-hexene
1,2-Epoxy-2-methylpropane
exo-2,3-Epoxynorbornane
1,2-Epoxyoctane
1,2-Epoxypentane
1,2-Epoxy-3-phenoxypropane
(2,3-Epoxypropyl)benzene
N-(2,3-Epoxypropyl)phthalimide
1,2-Epoxytetradecane
exo-3,6-Epoxy-1,2,3,6-tetrahydrophthalic anhydride
3,4-Epoxytetrahydrothiophene-1,1-dioxide
Isophorone oxide
Methyl-1,2-cyclopentene oxide
2-Methyl-2-vinyloxirane
α-Pinene oxide
Ethylene oxide
(±)-Propylene oxide
cis-Stilbene oxide
Styrene oxide
Tetracyanoethylene oxide
Tris(2,3-epoxypropyl) isocyanurate and combinations of two or more of the foregoing.

The quaternary ammonium salts may be made in one stage or two stages. The reaction may be carried out by contacting and mixing the amido amine with the olefin oxide in the reaction vessel wherein a carboxylic acid or alkyl phenol is added to the reaction mixture to provide a protonating agent. The carboxylic acid may be same acid used to make the amido amine or may be selected from any of the above listed fatty acids, formic acid, acetic acid, propionic acid, butyric acid, polymeric acid and mixtures thereof, such a polyolefinic mono- or di-carboxylic acid, polymeric polyacids and mixtures thereof, and the like. When used, the mole ratio of protonating agent per mole of epoxy equivalents added to the reaction mixture may range from about 0.5:10, for example from about 2:5, or from abut 1:2 to about 2:1 moles of acid per mole of epoxy equivalents. In one embodiment, the anion of the quaternary ammonium salt is a carboxylate anion.

The reaction may be carried out at temperature ranging from about 30° to about 90° C., for example from about 45° to about 70° C. The reaction may be conducted by reacting any amount of tertiary amino groups to epoxy groups sufficient to provide a quaternary ammonium compound. In one embodiment, a mole ratio of tertiary amino groups to epoxy groups may range from about 2:1 to about 1:2. When the amine component has an acid number ranging from about 1 to about 200 mgKOH/g, the reaction medium may include from about 0.5 moles to about 2.0 moles of carboxylic acid per mole equivalent of epoxide. When the reaction is completed volatiles and unreacted reagents may be removed from the reaction product by heating the reaction product under vacuum. The product is generally diluted with mineral oil, kerosene, or an inert hydrocarbon solvent to prevent the product from being too viscous.

In some aspects of the present application, the quaternary ammonium salt compositions of this disclosure may be used in combination with a fuel soluble carrier. Such carriers may be of various types, such as liquids or solids, e.g., waxes. Examples of liquid carriers include, but are not limited to, mineral oil and oxygenates, such as liquid polyalkoxylated ethers (also known as polyalkylene glycols or polyalkylene ethers), liquid polyalkoxylated phenols, liquid polyalkoxylated esters, liquid polyalkoxylated amines, and mixtures thereof. Examples of the oxygenate carriers may be found in U.S. Pat. No. 5,752,989, issued May 19, 1998 to Henly et. al., the description of which carriers is herein incorporated by reference in its entirety. Additional examples of oxygenate carriers include alkyl-substituted aryl polyalkoxylates described in U.S. Patent Publication No. 2003/0131527, published Jul. 17, 2003 to Colucci et. al., the description of which is herein incorporated by reference in its entirety.

In other aspects, the quaternary ammonium salt compositions may not contain a carrier. For example, some compositions of the present disclosure may not contain mineral oil or oxygenates, such as those oxygenates described above.

One or more additional optional compounds may be present in the fuel compositions of the disclosed embodiments. For example, the fuels may contain conventional quantities of nitrogen-containing detergents, octane improvers, corrosion inhibitors, cold flow improvers (CFPP additive), pour point depressants, solvents, demulsifiers, lubricity additives, friction modifiers, amine stabilizers, combustion improvers, dispersants, antioxidants, heat stabilizers, conductivity improvers, metal deactivators, marker dyes, cyclomatic manganese tricarbonyl compounds, and the like. In some aspects, the compositions described herein may contain about 10 weight percent or less, or in other aspects, about 5 weight percent or less, based on the total weight of the additive concentrate, of one or more of the above additives. Similarly, the fuels may contain suitable amounts of conventional fuel blending components such as methanol, ethanol, dialkyl ethers, 2-ethylhexanol, and the like.

Examples of suitable optional metal deactivators useful in the compositions of the present application are disclosed in U.S. Pat. No. 4,482,357 issued Nov. 13, 1984, the disclosure of which is herein incorporated by reference in its entirety. Such metal deactivators include, for example, salicylidene-o-aminophenol, disalicylidene ethylenediamine, disalicylidene propylenediamine, and N,N'-disalicylidene-1,2-diaminopropane.

Suitable optional cyclomatic manganese tricarbonyl compounds which may be employed in the compositions of the present application include, for example, cyclopentadienyl manganese tricarbonyl, methylcyclopentadienyl manganese tricarbonyl, indenyl manganese tricarbonyl, and ethylcyclopentadienyl manganese tricarbonyl. Yet other examples of suitable cyclomatic manganese tricarbonyl compounds are disclosed in U.S. Pat. No. 5,575,823, issued Nov. 19, 1996, and U.S. Pat. No. 3,015,668, issued Jan. 2, 1962, both of which disclosures are herein incorporated by reference in their entirety.

Commercially available detergents may be used in combination with the reaction products described herein. Such detergents include but are not limited to succinimides, Mannich base detergents, polyetheramine detergents, polyhydrocarbyl amine detergents, quaternary ammonium detergents, bis-aminotriazole detergents as generally described in U.S. patent application Ser. No. 13/450,638, and a reaction product of a hydrocarbyl substituted dicarboxylic acid, or anhydride and an aminoguanidine, wherein the reaction product has less than one equivalent of amino triazole group per molecule as generally described in U.S. patent application Ser. Nos. 13/240,233 and 13/454,697.

When formulating the fuel compositions of this application, the additives may be employed in amounts sufficient to reduce or inhibit deposit formation in a fuel system or combustion chamber of an engine and/or crankcase. In some aspects, the fuels may contain minor amounts of the above described reaction product that controls or reduces the formation of engine deposits, for example injector deposits in gasoline engines. For example, the gasoline fuels of this fuels of this disclosure may contain, on an active ingredient basis, an amount of the quaternary ammonium salt in the range of about 1 mg to about 100 mg of quaternary ammonium salt per Kg of fuel, such as in the range of about 5 mg to about 50 mg of per Kg of fuel or in the range of from about 5 mg to about 25 mg of the quaternary ammonium salt per Kg of fuel. In aspects, where a carrier is employed, the fuel compositions may contain, on an active ingredients basis, an amount of the carrier in the range of about 1 mg to about 100 mg of carrier per Kg of fuel, such as about 5 mg to about 50 mg of carrier per Kg of fuel. The active ingredient basis excludes the weight of (i) unreacted components associated with and remaining in the product as produced and used, and (ii) solvent(s), if any, used in the manufacture of the product either during or after its formation but before addition of a carrier, if a carrier is employed.

The additives of the present application, including the quaternary ammonium salt described above, and optional additives used in formulating the fuels of this invention may be blended into the base fuel individually or in various sub-combinations. In some embodiments, the additive components of the present application may be blended into the gasoline fuel concurrently using an additive concentrate, as this takes advantage of the mutual compatibility and convenience afforded by the combination of ingredients when in the form of an additive concentrate. Also, use of a concentrate may reduce blending time and lessen the possibility of blending errors.

The fuels of the present application may be applicable to the operation of gasoline engines. The engines include both stationary engines (e.g., engines used in electrical power generation installations, in pumping stations, etc.) and ambulatory engines (e.g., engines used as prime movers in automobiles). For example, the fuels may include any and all gasoline fuels, biorenewable fuels, gas-to-liquid (GTL) fuels, synthetic fuels, such as Fischer-Tropsch fuels, biomass to liquid (BTL) fuels, "Biorenewable fuels" as used herein is understood to mean any fuel which is derived from resources other than petroleum. Such resources include, but are not limited to, corn, maize, soybeans and other crops; grasses, such as switchgrass, miscanthus, and hybrid grasses; algae, seaweed, vegetable oils; natural fats; and mixtures thereof. In an aspect, the biorenewable fuel can comprise monohydroxy alcohols, such as those comprising from 1 to about 5 carbon atoms.

Non-limiting examples of suitable monohydroxy alcohols include methanol, ethanol, propanol, n-butanol, isobutanol, t-butyl alcohol, amyl alcohol, and isoamyl alcohol.

Accordingly, aspects of the present application are directed to methods for reducing the amount of engine deposits having at least one combustion chamber and one or more fuel injectors in fluid connection with the combustion chamber. In another aspect, the quaternary ammonium salts described herein may be combined with polyhydrocarbyl-succinimides, -Mannich compounds, -acids, -amides, -esters, -amide/acids and -acid/esters.

In some aspects, the methods comprise injecting a hydrocarbon-based fuel comprising quaternary ammonium salt of the present disclosure through the injectors of the engine into the combustion chamber, and igniting the fuel. In some aspects, the method may also comprise mixing into the fuel at least one of the optional additional ingredients described above. The fuel compositions described herein are suitable for both direct and port fuel injected engines.

In one embodiment, the fuels of the present application may be essentially free, such as devoid, of polyhydrocarbyl-succinimides, -Mannich compounds, -acids, -amides, -esters, -amide/acids and -acid/esters. In another embodiment, the fuel is essentially free of quaternary ammonium salts of a hydrocarbyl succinimide or quaternary ammonium salts of a hydrocarbyl Mannich compound. The term "essentially free" is defined for purposes of this application to be concentrations having substantially no measurable effect on injector cleanliness or deposit formation.

EXAMPLES

The following examples are illustrative of exemplary embodiments of the disclosure. In these examples as well as elsewhere in this application, all parts and percentages are by weight unless otherwise indicated. It is intended that these examples are being presented for the purpose of illustration only and are not intended to limit the scope of the invention disclosed herein.

Comparative Example 1

A commercial additive believed to be an alkoxylated quaternary ammonium salt made from a polyisobutylsuccinimide (PIBSI) which is prepared by reacting polyisobutylene succinic anhydride (PIBSA) and dimethylaminopropyl amine (DMAPA) according to U.S. Pat. No. 8,147,569.

Comparative Example 2

A quaternary ammonium salt was prepared by a method according to U.S. Pat. No. 8,147,569. A PIBSI (comparative example 1, about 210 g) was reacted with 1,2-epoxyhexane (36.9 g), acetic acid, (18.5 g) and 2-ethylhexanol (82 g) at a temperature of up to 90° C. for 3 hours. Volatiles were removed under reduced pressure to give the desired quaternary ammonium salt.

Inventive Example 1

A mixture of oleylamido propyl dimethylamine (150 g), 1,2-epoxy butane (59 g), acetic acid (37 g), and methanol (50 g) was heated slowly to 70° C. under an inert atmosphere. The mixture was gently refluxed at 70° C. for 2.5 hour. Volatiles were removed under reduced pressure to give the desired product as a brownish oil having a chlorine content that is undetectable.

Inventive Example 2

A mixture of oleylamido propyl dimethylamine (232 g), 1,2-epoxy butane (91 g), 2-ethylhexanoic acid (136 g), and methanol (93 g) was heated slowly to 70° C. under inert atmosphere. The mixture was gently refluxed at 70° C. for 1 hour, then 75° C. for 2 hours. Volatiles were removed under reduced pressure to give the desired product as a brownish oil.

Inventive Example 3

A quaternary ammonium salt was prepared similarly to that of Inventive Example 1 except that propylene oxide was used in place of 1,2-epoxy butane, and oleic acid was used in place of acetic acid. The reaction was carried out at about 50° C. in a pressured vessel. The resulting product was a brownish viscose oil.

Inventive Example 4

A quaternary ammonium salt was prepared similarly to that of Inventive Example 3 except that polyisobutylene succinic mono methyl ester acid was used in place of oleic acid to give product as a very viscose oil.

Inventive Example 5

A quaternary ammonium salt was prepared similarly to that of Inventive Example 3 except that ethylene oxide was used in place of propylene oxide.

Inventive Example 6

A quaternary ammonium salt was prepared similarly to that of Inventive Example 3, except that dodecyl phenol was used in place of oleic acid and 1,2-butylene oxide was used in place of propylene oxide. The resulting product was a brownish oil.

Inventive Example 7

A quaternary ammonium salt was prepared similarly to that of Inventive Example 6, except that dodecyl phenol was replaced with 3,5-di-tert-butyl-4-hydroxyhydrocinnamic acid $C_{7-9}$ branched alkyl ester. The resulting product was a brownish oil.

Inventive Example 8

A quaternary ammonium salt was prepared similarly to that of Inventive Example 4 except that (1) acetylamido propyldimethyl amine was used in place of oleylamido propyldimethylamine and (2) 1,2-butylene oxide was used in place of propylene oxide to give a product as a very viscose oil.

In the following example, a port fuel injector bench test was performed using one or more of the inventive examples and comparative examples as set forth below.

Port Fuel Injectors (PFI) Bench Test Protocol ASTM D6421 Modified

The following test method is a bench test procedure that was used to evaluate the tendency of automotive spark-ignition engine fuels to foul electronic port fuel injectors (PFI) in a spark ignition engine. The test method used a bench apparatus equipped with Bosch injectors specified for use in a 1985-1987 Chrysler 2.2-L turbocharged engine. The test method was based on a test procedure developed by the Coordinating Research Council (CRC Report No. 592) for predicting the tendency of spark-ignition engine fuel to form deposits in small metering clearances of fuel injectors in a port fuel injection engine. Fuel injector fouling was calculated according to the following equation:

$$F_o = \frac{F_1 - F_2}{F_1} \times 100$$

where $F_0$ is the percent fouling, $F_1$ is an initial flow mass in tenths of a gram, and $F_2$ is a flow mass at the end of the test in tenths of a gram. The percent fouling was calculated for each injector for three flow mass readings and the average of four injectors was reported in percent.

TABLE 1

| Run No. | Additives and treat rate (ppm by weight) | Average % Fouling ($F_o$) |
|---|---|---|
| 1 | Base Fuel | 54.5 |
| 2 | Base Fuel Plus Conventional Mannich Detergent[1] (75 ppmw) | 21.44 |
| 3 | Base Fuel Plus Compound of Inventive Example 3 (75 ppmw) | 0.73 |
| 4 | Base Fuel Plus Compound of Inventive Example 4 (75 ppmw) | 1.17 |

[1]Reaction product of dibutylamine, polyisobutylene cresol (1000 $MW_n$) and formaldehyde as generally described in U.S. Pat. No. 7,491,248.

As shown by the foregoing table, a fuel containing the compound of Inventive Examples 3 and 4 provided significant improvement in injector fouling in a port fuel injected gasoline engine as compared to the base fuel without any detergent and as compared to the same base fuel containing a conventional Mannich detergent.

An engine test measuring fuel injector deposit (referred to as "DIG test") was performed following a procedure disclosed in Society of Automotive Engineer (SAE) International publication 2009-01-2641 "Test and Control of Fuel Injector Deposits in Direct Injected Spark Ignition Vehicles". A mathematical value of Long Term Fuel Trim (LTFT) was used to gauge the ability of additive to keep deposit from accumulating in the injectors, or to keep injectors clean. The higher the LTFT, the more deposit in the injectors and the less effective is the additive in keeping injectors clean.

The test may also be used to gauge the effectiveness of additives to clean up the injectors in a gasoline engine by running a standard 48 hour dirty up phase followed by a 48 hour clean up phase.

For the DIG test, a 2008 General Motors Pontiac Solstice GXP equipped with a DISI 2.0 liter turbocharged 1-4 engine was used. The results are shown in the following table.

TABLE 2

| Run No. | Additives and treat rate (ppm by weight) | Normalized LTFT % |
|---|---|---|
| 1 | Gasoline with no additive | 8.0 |
| 2 | Gasoline with typical Mannich detergent[2] (81 ppmw) | 9.3 |
| 3 | Fuel and additive of Run 2 plus 8 ppm of Inventive Example 3 | −1.6 |
| 4 | Fuel and additive of Run 2 plus 8 ppm of Inventive Example 4 | 1.5 |

[2]Mannich detergent as described in Table 1.

Run 1 showed the effects of gasoline with no additive on injectors in a direct injected gasoline engine. Run 2 showed that gasoline containing a conventional Mannich detergent was not effective to keep the fuel injectors clean. Runs 3 and 4 showed that small amounts of the quaternary ammonium salts of Examples 3 and 4, respectively, added to a fuel composition of Run 2 was sufficient to keep the fuel injectors clean. The foregoing table of data demonstrates the substantial durability of the keep clean properties of the additives of the disclosure.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A gasoline fuel composition comprising from about 1 to about 100 ppm of a fuel soluble additive for a fuel injected gasoline engine based on a total weight of the fuel composition, the fuel soluble additive comprising a quaternary ammonium salt derived from an amido amine containing at least one tertiary amino group and an epoxide, in the presence of a proton donor, wherein the amido amine is made in a reaction medium that is substantially devoid of an acylating agent.

2. The gasoline fuel composition of claim 1, wherein the proton donor is selected from the group consisting of a carboxylic acid and an alkyl phenol.

3. The gasoline fuel composition of claim 1, wherein the amine comprises an amido amine derived from a acid having from about 1 to about 54 carbon atoms.

4. The gasoline fuel composition of claim 1, wherein the epoxide is selected from the group consisting of a hydrocarbyl epoxide of the formula

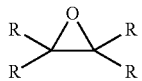

wherein each R is independently selected from H and a $C_1$ to $C_{50}$ hydrocarbyl group, and polyepoxides.

5. The gasoline fuel composition of claim 1, wherein the hydrocarbyl epoxide is selected from the group consisting of styrene oxide, ethylene oxide, propylene oxide, butylenes oxide, 1,2-epoxycyclohexane, 2,3-epoxy-5-methylhexane, stilbene oxide, and $C_5$ to $C_{200}$ epoxides.

6. The gasoline fuel composition of claim 2, wherein the proton donor is a carboxylic acid selected from the group consisting of fatty acids, formic acid, acetic acid, propionic acid, butyric acid, polyisobutenyl succinic acid, amide/acid, or acid/ester, and polymeric acids, and mixtures thereof.

7. The gasoline fuel composition of claim 1, wherein the fuel composition comprises from about 5 to about 50 ppm of the fuel soluble additive based on a total weight of the fuel composition.

8. A method of improving the injector performance of a fuel injected gasoline engine comprising operating the engine on a fuel composition comprising a major amount of gasoline fuel and from about 5 to about 100 ppm by weight based on a total weight of the fuel composition of a quaternary ammonium salt derived from an amido amine containing at least one tertiary amino group and an epoxide, in the presence of a proton donor selected from the group consisting of a carboxylic acid and an alkyl phenol, wherein the amido amine is made in a reaction medium that is substantially devoid of an acylating agent.

9. The method of claim 8, wherein the engine comprises a direct injected gasoline (DIG) engine.

10. The method of claim 8, wherein the engine comprises a port fuel injected (PFI) engine having an average fuel flow loss of less than 10 percent in a port fuel injection test.

11. The method of claim 8, wherein the amido amine is derived from a fatty acid.

12. The method of claim 8, wherein the amido amine is derived from an acid having from about 1 to about 54 carbon atoms.

13. The method of claim 8, wherein the epoxide is selected from the group consisting of a hydrocarbyl epoxide of the formula

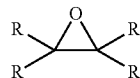

wherein each R is independently selected from H and a $C_1$ to $C_{50}$ hydrocarbyl group, and polyepoxides.

14. The method of claim 8, wherein the proton donor is a carboxylic acid selected from the group consisting of fatty acids, formic acid, acetic acid, propionic acid, butyric acid, polyisobutenyl succinic acid, amide/acid, or acid/ester, and polymeric acids, and mixtures thereof.

15. The method of claim 8, wherein the fuel composition contains from about 10 to about 50 ppm of the quaternary ammonium salt based on a total weight of the fuel composition.

16. A method of operating a fuel injected gasoline engine comprising combusting in the engine a fuel composition comprising a major amount of fuel and from about 5 to about 100 ppm by weight based on a total weight of the fuel composition of a quaternary ammonium salt derived from an amido amine containing at least one tertiary amino group and an epoxide, in the presence of a proton donor selected from the group consisting of a carboxylic acid and an alkyl phenol, wherein the amido amine is made in a reaction medium that is substantially devoid of an acylating agent.

17. The method of claim 16, wherein the amido amine is derived from a fatty acid.

18. The method of claim 16, wherein the engine comprises a direct injected gasoline (DIG) engine.

19. The method of claim 16, wherein the engine comprises a port fuel injected (PFI) engine.

* * * * *